US008496971B2

(12) United States Patent
Gradl et al.

(10) Patent No.: US 8,496,971 B2
(45) Date of Patent: Jul. 30, 2013

(54) TREATMENT OF OSTEOPOROSIS

(75) Inventors: Georg Gradl, Rostock (DE); Detlef Behrend, Warnemünde (DE); Klaus-Peter Schmitz, Warnemünde (DE); Katrin Sternberg, Rostock (DE); Kathleen Schmohl, Rostock (DE); Sven Kramer, Rostock (DE)

(73) Assignee: Universitaet Rostock, Rostock (DE)

( * ) Notice: Subject to any disclaimer, the term of this patent is extended or adjusted under 35 U.S.C. 154(b) by 597 days.

(21) Appl. No.: 12/445,635

(22) PCT Filed: Oct. 16, 2007

(86) PCT No.: PCT/DE2007/001853
§ 371 (c)(1),
(2), (4) Date: Oct. 11, 2010

(87) PCT Pub. No.: WO2008/046405
PCT Pub. Date: Apr. 24, 2008

(65) Prior Publication Data
US 2011/0027381 A1 Feb. 3, 2011

(30) Foreign Application Priority Data

Oct. 16, 2006 (DE) .................. 10 2006 048 833

(51) Int. Cl.
*A01N 59/26* (2006.01)
*A61K 33/42* (2006.01)
(52) U.S. Cl.
USPC ........................................................ 424/602
(58) Field of Classification Search
None
See application file for complete search history.

(56) References Cited

U.S. PATENT DOCUMENTS

| 4,623,553 | A | 11/1986 | Ries et al. | 427/2 |
| 5,015,677 | A | 5/1991 | Benedict et al. | 524/17 |
| 5,320,844 | A | 6/1994 | Liu | 424/422 |
| 5,583,114 | A | 12/1996 | Barrows et al. | 514/21 |
| 6,187,047 | B1 | 2/2001 | Kwan et al. | 623/16.11 |
| 6,319,712 | B1 | 11/2001 | Meenen et al. | 435/395 |
| 6,485,751 | B1 | 11/2002 | Wang | 424/499 |
| 6,509,409 | B1 * | 1/2003 | Thetford | 524/589 |
| 2002/0095020 | A1 | 7/2002 | Hucks et al. | 528/196 |
| 2003/0087338 | A1 | 5/2003 | Messersmith et al. | 435/68.1 |
| 2003/0180376 | A1 * | 9/2003 | Dalal et al. | 424/602 |
| 2004/0249015 | A1 | 12/2004 | Jia et al. | 523/115 |
| 2005/0199549 | A1 | 9/2005 | Goerlitzer et al. | 210/638 |
| 2009/0280179 | A1 | 11/2009 | Neumann et al. | 424/484 |

FOREIGN PATENT DOCUMENTS

| DE | 19958526 A1 | 6/2000 |
| EP | 0164483 B1 | 6/1984 |
| EP | 1221454 A1 | 7/2002 |
| EP | 1497340 B1 | 1/2005 |
| EP | 1518569 A1 | 3/2005 |
| EP | 0947142 B1 | 8/2005 |
| WO | WO 93/12736 A1 | 7/1993 |
| WO | WO 94/28937 A1 | 12/1994 |
| WO | WO 96/03159 A1 | 2/1996 |
| WO | WO 2006/031196 A1 | 3/2006 |
| WO | WO 2007/090373 A2 | 8/2007 |

OTHER PUBLICATIONS

Burton et al., "Vertebroplasty and Kyphoplasty," *Pain Physician* 6(3): 335-354, 2003.
Ellis-Behnke et al., "Nano hemostat solution: immediate hemostasis at the nanoscale," *Nanomedicine: Nanotechnology, Biology, and Medicine* 2, 2006, in press, pp. 1-9.
Jobmann et al., "End-group functionalized polylactides: a potential protein carrier," *Journal of Controlled Release* 41(1): 8-8(1), Aug. 1996 [abstract only, p. S8].
Kreiser-Saunders et al., "Zn lactate-catalyzed copolymerization of L-lactide with glycolide or ε-caprolactone," *Macromol. Chem. Phys.* 199: 1081-1087, 1998.
Kricheldorf et al., "Polylactones: 31. Sn(II)octoate-initiated polymerization of L-lactide: a mechanistic study," *Polymer* 36(6): 1253-1259, 1995.
Kricheldorf et al., "Polylactides—Synthesis, Characterization and Medical Application," *Macromol. Symp.* 103: 85-102, 1996.
Kricheldorf et al., "Resorbable Initiators for Polymerizations of Lactones," *Macromol. Symp.* 144: 269-276, 1999.

* cited by examiner

*Primary Examiner* — James H. Alstrum-Acevedo
*Assistant Examiner* — Thor Nielsen
(74) *Attorney, Agent, or Firm* — Seed IP Law Group PLLC

(57) ABSTRACT

The present invention relates to a combination for the treatment of osteoporosis and/or the prophylaxis and treatment of bone fractures, said combination comprising collagen, an additional peptide, a calcium-containing substance and a wetting agent with a terminally functionalized oligolactone. The invention also relates to artificial bones and implants produced by the combination and to the use of said combination for fixing implants and treating osteoporosis and/or the prophylaxis and treatment of bone fractures. The invention further relates to a method for producing artificial bones and implants.

21 Claims, No Drawings

TREATMENT OF OSTEOPOROSIS

The present invention relates to a combination of components for the treatment of osteoporosis and/or for the prophylaxis and treatment of bone fractures, which comprises collagen, additional peptide, a calcium-containing substance and a crosslinker. The invention also relates to artificial bones and implants produced from the combination and to the use of the combination for fixing implants and for the treatment of osteoporosis and/or prophylaxis and treatment of bone fractures. The invention further relates to a process for producing artificial bones and implants.

Osteoporosis is a disorder leading to excessive breakdown of the bone substance and structure, and it is associated with increased susceptibility to fractures relating to the whole skeleton. Initially, osteoporosis progresses imperceptibly but, in the case of bone fractures, the disorder means, especially in elderly people, a high morbidity with pain, confinement to bed and in some cases permanent immobilization. Osteoporosis is a common pathological condition. In Germany alone, about 8 million people suffer therefrom.

A distinction is made between primary and secondary osteoporosis. Primary osteoporosis includes post-menopausal osteoporosis and osteoporosis of the aged (involutional osteoporosis). Almost half of all women over 50 years of age show a reduction in bone density, of whom in turn 50% develop manifest osteoporosis. For men over 70 years of age, osteoporosis of the aged is likewise a common pathological condition.

Secondary osteoporosis occurs inter alia as a consequence of metabolic disorders or hormonal impairments.

Osteoporotic bone breaks under slight stress, such as minimal trauma or even the load of the person's body weight. The fracture is difficult to treat. Bone fractures associated with osteoporosis mainly occur in the neck of the femur, in the wrist and in the vertebrae of the spinal column. Compression fractures of the vertebrae (vertebral compression fractures, VCFs) are for example common. They are associated with a decrease of at least 15% in the size of the vertebra. 84% of such fractures are associated with pain, especially intense pain at the site of the fracture, which persists for about 4 to 6 weeks. Chronic pain is a common occurrence if there is serious collapse of a layer, or a plurality of layers are compressed. Lung problems, loss of mobility and less exercise tolerance are general consequences. These are often associated with chronic depression, which may exacerbate the chronic pain associated with the deformity. The consequences of fractures may be permanent, especially in elderly people. They often lead to deaths through secondary disorders such as pneumonia or pulmonary embolism.

Medicaments such as calcium and vitamin D, and biphosphonates, are able to strengthen the bone substance slowly. This takes a long time in severe osteoporosis and may not have local effects on regions of bone at particular risk of fracture. It is also possible to counteract osteoporosis by movement, because the bone material and in particular the bone strength is increased through the maximum forces occurring during movement. This is also a slow process, and, in severe osteoporosis, attention must be paid to the mobility restricted in some cases, and the risk of fracture.

Fractures associated with osteoporosis, especially vertebral fractures, can be treated with minimally invasive techniques such as vertebroplasty and kyphoplasty. It is usual in this connection to puncture the bone with thin needles and fill it with a material which is initially pasty/fluid, and which sets in the interior of the bone and then stabilizes the latter from inside (vertebroplasty). Bone cement in various configurations is available for this purpose (e.g.) PALACOS®, and biodegradable cement has recently become available. The synthetic polymer polymethylmethacrylate (PMMA) is generally used for this purpose. Kyphoplasty is the use of balloons which can be unfolded in a collapsed vertebra to produce a cavity before injection of cement. Stabilization of fractures by these methods often leads to a decrease in pain. The risks are slight, but neverless serious complications occur. Thus, PMMA may exit from the vertebrae, with systemic consequences. There may be compression of the spinal cord or the nerves, embolisms in veins and lung, or even complete circulatory collapse (Burton et al., 2003, Vertebroplasty and Kyphoplasty, Pain Physician 6:335-343).

There is thus a need to develop alternative methods and products for stabilizing bones in osteoporosis, especially those which are well tolerated and can also be employed for prophylaxis of bone fractures.

This problem is solved by the present invention, especially by the subject matter of the claims.

The present invention in particular provides a combination for the treatment of osteoporosis and/or for the prophylaxis and treatment of bone fractures comprising at least one peptide, in particular collagen, a calcium-containing substance and a crosslinker. The crosslinker comprises terminally functionalized oligolactone as a bridge molecule. In one embodiment, the crosslinker further includes a catalyst of the crosslinking reaction. The crosslinker is suitable for crosslinking the peptide or collagen and, where appropriate, further substrates comprising suitable functional groups, in particular amino groups (e.g. oligopeptides).

Collagen is well known as a structural protein of human and animal bone in the form of a triple helix. The collagen used in the context of the invention may be a collagen hydrolysate, e.g. gelatin. It may be recombinantly prepared or of animal origin, for instance bovine or porcine collagen. A collagen powder is preferably employed, but the collagen can also already be in the form of a suspension or solution or of a preshaped matrix.

The preparation preferably comprises about 10-70% by weight collagen, in particular about 20-50% by weight collagen or about 30% by weight collagen (the percentage data are based on the total mass without solvent).

Collagen contains a large number of functional groups, e.g. amino groups of lysine, which can be crosslinked.

In order to accelerate the crosslinking and thus setting of the preparation, preferably, a further biopolymer which contains a large number of functional groups making crosslinking possible, e.g. free amino groups, is added. The biopolymer advantageously is non-toxic and/or biodegradable. The biopolymer preferably is a protein, peptide or oligopeptide, these expressions being used as synonyms in the context of the present invention. The peptide comprises at least two amino groups and/or hydroxyl groups, in particular at least one, preferably two or more diamino acids and/or hydroxyl groups.

In the context of the present invention, peptide refers both to an oligopeptide (2 to about 100 amino acids in length) and to a protein (protein about 100 to about 5000 amino acids in length, preferably with a length of about 100-1000 or 100-200 amino acids). The peptide preferably has a length of 4-100 amino acids, in particular 10-20 amino acids. The peptide may have a molecular weight of about 1 kDa to about 100 kDa or up to about 200 kDa, in particular about 2 kDa to about 50 kDa or about 5 kDa to about 20 kDa. It may be modified or substituted, e.g. glycosylated. In addition to the usual proteinogenic amino acids, the oligopeptide may also comprise modified or untypical amino acids such as hydroxylysine.

The use of D-amino acids instead of L-amino acids or in addition thereto is possible and retards the breakdown of the peptide.

It is, of course, also possible for a plurality of different peptides of these types or further biopolymers to be present. This variant is not specifically mentioned hereinafter, but is always included.

The reactive amino groups may be primary or secondary amino groups. At least one of the reactive amino groups of the peptide preferably is part of a diamino acid. The peptide therefore preferably comprises at least one diamino acid, preferably at least 2, 3, 4, 5 or more diamino acids. It is possible to employ lysine-containing peptides (or oligopeptides or proteins).

Other amino acids such as arginine, asparagine, glutamine or histidine have reactive amino groups able to react with the oligolactones.

The reactive amino groups, in particular the amino groups provided by the diamino acid, are particularly suitable for the crosslinking reaction between peptide and oligolactone. Hydroxyl groups in the peptide may also contribute to the crosslinking reaction. The peptide therefore preferably comprises at least one amino acid having a hydroxyl group, that is in particular serine, threonine or tyrosine. It is also possible for hydroxylysine or polyphenolic amino acid units like those present in the MAPs to occur in the peptides employed according to the invention. One advantage of the present invention, however, is that the presence of these specific amino acid units and thus the use of MAPs is not necessary. For example, recombinant preparation is therefore straightforwardly possible for the peptides used.

The crosslinking resulting from the reaction of the oligolactones with the peptide substantially depends on the content of available reactive groups in the peptide. Particularly good adhesive properties can be achieved with a molar proportion of amino acids having a free amino group (e.g. diamino acids such as lysine) and/or hydroxyl group of at least 10% in the peptide. However, the proportion of these amino acids preferably is higher, at least 20%, at least 30%, at least 40 or at least 50% or even at least 80 to 100%. These criteria are satisfied by naturally occurring peptides and proteins. Particularly suitable examples are MAPs.

It is, however, also possible to employ particularly suitable shorter peptides which can easily be prepared artificially. In a particularly preferred embodiment of the invention, about 50% of the amino acids of the peptide are lysine and/or about 50% of the amino acids of the peptide are tyrosine. These may for example be arranged as a repeating dipeptide unit. About 50% means approximately 40-60%. A different sequence or inclusion of further amino acids, especially arginine, asparagine, glutamine or histidine (instead of lysine or additionally), serine or threonine (instead of tyrosine or additionally) is also straightforwardly possible. A length of the peptide of approximately 10-20 amino acids is particularly preferred. It has been possible to achieve excellent results for instance with peptides with a length of 10-20 amino acids which consisted of repeating dipeptide units of lysine and tyrosine ([Lys-Tyr]$_n$ or [Tyr-Lys]$_n$, n=5 to n=10).

The product preferably comprises 0 to about 40% by weight additional peptide, in particular about 10-30% by weight or about 20% by weight.

In a further embodiment it is moreover additionally possible for the combination of the invention to comprise chain extenders for bulk polymerization (selected from a group comprising diols, diamines, oligolactones such as EOL, EOG, GOL, GOLG, POL). The presence of such an additional chain extender is, however, not absolutely necessary.

The calcium-containing substance used in the context of the invention preferably is calcium phosphate, for example tricalcium orthophosphate and/or hydroxylapatite. The preparation preferably comprises about 20-90% by weight calcium-containing substance, in particular about 40-80% by weight calcium-containing substance, about 50-70% by weight calcium-containing substance, or about 60-65% by weight calcium-containing substance.

It is also possible to use a combination with a smaller proportion of calcium-containing substance, but this does not achieve the hardness which is particularly advantageous for use as "liquid bone" or bone cement.

It is preferred for collagen and/or additional peptide and calcium-containing substance already to be mixed in the combination, but they may also be present separately.

The crosslinker comprises a molecule which is able to form bridges between the collagen and thus to stabilize and consolidate the mixture. This is preferably a functionalized oligolactone, in particular a terminally functionalized oligolactone.

In the context of the invention, oligolactones refer to "inner esters" of hydroxy carboxylic acids and, thus, in a broader sense, also to oligoglycolides, oligolactides and copolymers thereof, which, as known in the prior art, can be prepared by ring-opening polymerization. Terminally functionalized oligolactones mean polymers of hydroxy carboxylic acids having a central at least dihydric alcohol, with the hydroxyl groups of the alcohol being esterified with lactones or lactides or glycolides by ring opening, and with the free ends of the polyesters having reactive functional groups. One example is depicted in reaction scheme 1.

The oligolactone preferably has terminal isocyanate groups. Functionalization with aldehyde or epoxide groups is also possible, and the resulting product may achieve an adhesive effect in the combination of the invention. It has surprisingly been found that both an increased strength of the polymer and a greater adhesion are achieved by functionalizing the oligolactones with isocyanate.

The oligolactone preferably is an ethylene glycol oligolactide (EOL) as depicted in reaction scheme 1. In one embodiment of the invention, n is 1 (when 1 part of ethylene glycol is reacted with 2 parts of lactide, i.e. 1/2 is M=350.3 g/mol), but n may also be 2, 3, 4 or 5. As the number of units increases, there is an increase in the viscosity of the oligolactone, and of the adhesives obtained in a reaction with the peptides. Optimal manipulability has been achieved with oligolactones (n=1), because satisfactory processing with a low solvent content was ensured thereby. In addition, further ethylene glycol derivatives such as ethylene glycol oligoglycolide (EOG 1/2, M=294.2 g/mol) have been provided with terminal isocyanate groups. Good adhesive properties were obtained with these derivatives too.

It is also possible analogously to use further oligolactones, for instance based on polymerization products of glycerol and pentaerythritol. Thus, for example, reaction of pentaerythritol oligolactide (POL 1/4, M=712.6 g/mol), glycerol oligolactide (GOL 1/0.5, M=164.1 g/mol) and glycerol oligolactide-co-glycolide (GOLG 1/1/3, M=584.4 g/mol) with hexamethylene diisocyanate (HDI) results in the following products with terminal isocyanate groups: POL-NCO, EOG-NCO and GOLG-NCO.

Reaction Scheme 1

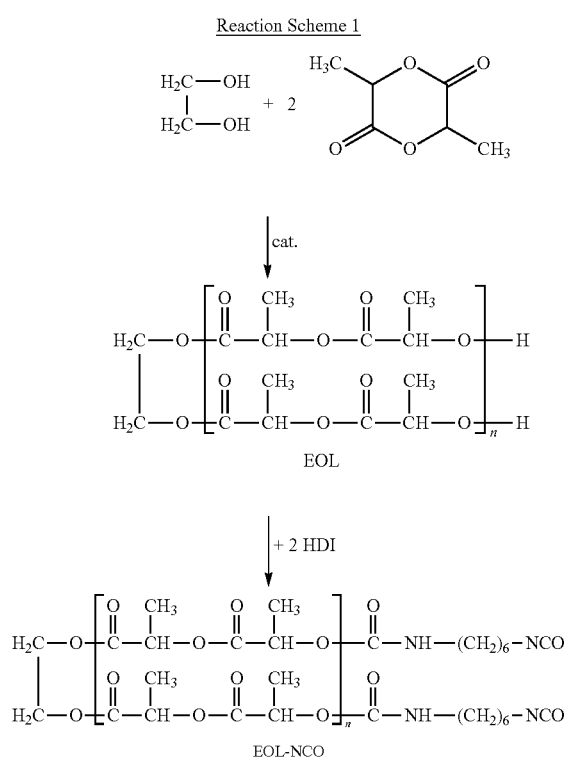

EOL

↓ + 2 HDI

EOL-NCO

It is, of course, also possible to employ a plurality of different oligolactones. This variant is not specifically mentioned hereinafter, but is always included.

It is possible to employ organic metal compounds, for instance zinc or tin compounds, as catalyst for preparing the oligolactones (Kricheldorf, H. R., Kreiser-Saunders, I., Boettcher, C.: "Polylactones: 31. Sn(II)octoate-initiated polymerization of L-lactide: a mechanistic study", in: Polymer Vol. 36 No. 6, pp. 1253-1259, 1995; Kreiser-Saunders, I., Kricheldorf, H. R.: "Polylactones: 39$^a$. Zn lactate-catalyzed copolymerisation of L-lactide with glycolide or ε-caprolactone", in: Macromol. Chem. Phys. 199, 1081-1087, 1998; Kricheldorf, H. R., Kreiser-Saunders, I., Damrau, D. O: "Resorbable Initiators for Polymerization of Lactones", in: Macromol. Symp. 144, 269-276, 1999; Kricheldorf, H. R., Kreiser-Saunders, I.: "Polylactides-Synthesis, Characterization and Medical Application", in: 103, 85-102, 1996).

Examples are zinc(II) and tin(II) salts of organic carboxylic acids, e.g. zinc(II) octoate, zinc(II)ethylhexoate, tin(II) acetate, tin(II) octoate, tin(II) ethylhexoate and tin(II) laurate, and dialkyltin(IV) salts of organic carboxylic acids, e.g. dibutyltin diacetate, dibutyltin dilaurate, dibutyltin maleate and dioctyltin diacetate. A further possibility is also to use iron (III) salts such as, for example, iron(III) chloride.

In order to increase the biocompatibility, the catalysts of this reaction are preferably removed before use of the oligolactones, so that they are present in amounts of less than 0.1%, preferably of less than 0.01%. Methods for doing this are known in the prior art (EP1497340, EP1221454).

Alternatively or additionally, especially for producing medical devices, the zinc compounds or iron compounds with better biocompatibility are employed.

The oligolactones can be reacted with diisocyanates, e.g. with hexamethylene diisocyanate, in order to prepare oligolactones having terminal isocyanate groups. Aliphatic isocyanates are preferably used for the reaction, because carcinogenic diamines may be formed from aromatic diisocyanates. Purification is unnecessary in the case of stoichiometric reaction. Where appropriate, however, purification can be carried out, e.g. by distillation.

The medical product of the invention preferably includes about 0.1 to 40% by weight crosslinker, in particular about 1 to 30% by weight, about 2 to 20% by weight or 5 to 10% by weight crosslinker. It is preferred in this context that at least 70% by weight, at least 80% by weight, at least 90 or at least 95 or 99% by weight of the crosslinker are terminally functionalized oligolactone.

If rapid setting is desired, the crosslinker includes a catalyst of the crosslinking reaction. The catalyst is able to bring about a crosslinking between the collagen molecules and/or further peptides and molecules having reactive functional groups. This crosslinking may be a direct crosslinking, e.g. via disulfide bridges, or an indirect crosslinking via a bridge molecule. In the latter case, the catalyst mediates the reaction between collagen and/or additional peptide and oligolactone.

The proportion of catalyst in the crosslinker is 0-about 20% by weight, preferably about 0.05-10% by weight, about 0.1-8% by weight, about 1-6% by weight or about 3-5% by weight.

Catalysts accelerate the reaction rate of a chemical reaction without themselves being consumed therein. An acceleration (for instance by a factor of 10-100) is often worthwhile, also depending on the starting materials and the exact area of use. However, a slower reaction rate may also be preferred so that, for example, a longer time is available for processing. Especially when additional oligopeptides with a high proportion (at least 30%, preferably at least 50%) of amino acids having reactive amino groups, preferably diamino acids, are employed, the reaction rate even without catalyst is so high that the latter is unnecessary for rapid setting. A particularly rapid setting is achieved with catalyst with these peptides.

Preferably, it is possible with the product of the invention that firm setting can take place in a period of from about 30 seconds to 15 minutes, better of about 1 to 5 minutes. However, it is unnecessary for all the components to have reacted completely, i.e. a complete bulk polymerization to have taken place, in this time; on the contrary, it is sufficient to achieve a firmness with which the bonded substrates are fixed. The reaction with catalyst substantially proceeds to completion in a period of approximately 3-60 minutes, preferably approximately 3-10 minutes; without catalyst the period for the reaction substantially to proceed to completion is approximately 30 minutes to several days, preferably approximately 30-120 minutes.

It is possible to employ as catalyst for instance a basic amine, an amidine, advantageously 2,3-dimethyl-3,4,5,6-tetrahydropyrimidine, a tertiary amine, advantageously triethylamine, tributylamine, dimethylbenzylamine, N-methyl-, N-ethyl-, -cyclohexylmorpholine, N,N,N', N'tetramethylethylenediamine, N,N,N',N'diaminoethyl ether, bis(dimethylaminopropyl)urea, dimethylpiperazine, 1,2-dimethylimidazole, 1-azabicyclo(3,3,0)octane and preferably 1,4-diazabicyclo(2,2,2)-octane and/or an alkanolamine such as triethanolamine, triisopropanolamine, N-methyl- and N-ethyldiethanolamine and dimethylethanolamine, preferably 1,4-diaza[2.2.2]bicyclooctane)(DABCO®. The catalyst preferably is 1,4-diaza[2.2.2]bicyclooctane (DABCO®).

In a particularly preferred embodiment, the combination comprises collagen, a calcium-containing substance, in particular hydroxylapatite, an oligolactone, in particular ethylene glycol oligolactide with terminal isocyanate groups and the catalyst 1,4-diaza[2.2.2]bicyclooctane (DABCO®), where appropriate with the addition of a further peptide.

The combination may comprise active substances which, as long as they are able to react with the components, can be fixed at the site of use and there act permanently. Conceivable examples are antibiotics, further antimicrobial active substances and/or substances which inhibit or promote the immune system and/or messengers which promote the buildup of bone substance and/or inhibit breakdown thereof. It is possible for further additives and auxiliaries to be present, e.g. fillers such as albumin, hyaluronic acid or the like. Additives such as thixotropic agents, e.g. nanodisperse calcium phosphates (e.g. beta-tricalcium phosphate (beta-TCP)) or nanodisperse silicas, can be used to adapt the viscosity and flowability.

In one embodiment of the invention, one or more of the components of the combination are present separate from one another. It is possible for example for all the components to be present separately. However, it is also possible for components to be premixed to prepare for use; for example, collagen/peptide and calcium-containing substance may already be mixed. A prepared mixture of one or more of these components which includes the catalyst can also generally be stored satisfactorily. Storage at about 4° C. is advisable. However, it is advantageous for the oligolactone and collagen and/or additional biopolymer/peptide to be mixed only when the reaction between the two is desired. If, however, the catalyst is added only immediately before use, a mixture which includes both collagen or biopolymer and oligolactone can also be stored.

One or more components of the combination can—together or separately—be taken up in one or more solvents. The solvent is preferably non-toxic and, in small quantities, biocompatible. It may be an aqueous solvent, e.g. phosphate buffer, in particular a calcium phosphate buffer, or an organic solvent such as DMSO, especially on use of oligolactones functionalized with isocyanate, or a mixture thereof. In one embodiment, the solvent used is a mixture of DMSO and water (or buffer), in which case the proportion of water is about 5-20%, preferably about 8-12% or about 10%. The collagen/peptide (and where appropriate the catalyst) is in particular dissolved in the aqueous or water-containing solvent, and the oligolactone in DMSO.

In one embodiment, the preparation is already prepared for use in a two-component dispenser, preferably already with attached mixing extruder, wherein one component comprises collagen/peptide and, where appropriate, the catalyst, and the other component the oligolactone. This permits particularly accurate dosage and simple handling. A double-chamber dispenser for instance of the Mixpac type (Mixpac Systems AG, Rotkreuz, Switzerland) is preferred.

Alternatively, the combination or its constituents can be taken up in a solvent immediately before use.

The constituents of the combination are preferably already present in a ratio of amounts which is appropriate for the use thereof and saves troublesome dosage of the ingredients. The components are preferably packaged in a sterile manner.

Sterilization of the product of the invention or of its individual components can advantageously be achieved without structural alteration, e.g. by sterile filtration of solutions. However, sterilization by gamma radiation is preferred, because this is possible after packaging and thus aseptic filling is unnecessary. It has been possible to show that the structure of the functionalized lactones is retained on gamma sterilization.

The combination of the invention preferably is a medical product suitable for the treatment of osteoporosis and/or for the prophylaxis and treatment of bone fractures. Classification as pharmaceutical product, however, depending on national law, is likewise possible. The terms medical product and pharmaceutical product are exchangeable for the purposes of the description of the invention.

The invention also relates to a product in which the above-mentioned components are mixed together, and the collagen, where appropriate with inclusion of further biopolymers, is crosslinked to itself. It is preferred for the collagen, where appropriate with inclusion of further reactive substrates, to be crosslinked to itself via the oligolactone used in the context of the invention. Herein, it is possible, but not necessary, for a complete reaction to take place, as long as an adequate strength of the set product is achieved.

Such a product may be in the form of an artificial bone, bone part, or implant, in particular for bone fracture stabilization, or in the form of an implant coating. Such an implant in particular is a nail, a plate, a screw, a pin, a prosthesis, a hip socket, a vertebra substitute or a cage (cage as vertebra substitute).

The products produced in this way resemble human or animal bone in their consistency and, therefore, and because of their good biocompatibility, they are outstandingly suitable for implantation and can be used instead of the previously used steel or titanium implants or can be combined with the latter. Inter alia, the combination is suitable for coating implants made of other materials. For this purpose, plasma-coating methods are also contemplated.

The invention also relates to the use of the described combination in combination with implants made of other materials, e.g. titanium. The combination of the invention is in this case used instead of conventional bone cement and fixes the implant.

The invention further relates to a medical product which comprises the components described above and is suitable for the treatment of osteoporosis and/or for the prophylaxis and treatment of bone fractures, and to the use of the combination described above for the treatment of osteoporosis and/or for the prophylaxis and treatment of bone fractures. It is in particular intended for osteoporotic bones to be stabilized prophylactically when there is a threat of fracture. However, a use may also be worthwhile if the bone density is reduced, or with other disorders associated with an increased risk of fractures, e.g., for osteogenesis imperfecta.

For use, the components of the combination are mixed together and brought into contact with bone. The components of the combination are preferably mixed with a solvent and injected in liquid or pasty form into the bone. The product sets there.

The invention likewise relates to a corresponding method for the treatment of osteoporosis and/or for the prophylaxis and treatment of bone fractures.

The invention therefore for the first time provides a "liquid bone", which is not prepared on the basis of synthetic polymers, but on the basis of crosslinked collagen. In a preferred embodiment, the combination of the invention thus does not comprise PMMA or other acrylates.

On use, preferably a minimally invasive technique is used. The crosslinking of the collagen and combining with the calcium-containing substance and with the surrounding bone material stabilizes the bone.

The combination can not only be used for bones at risk of fracture as part of prophylaxis of fractures, but also when a fracture has already taken place as part of the surgical management thereof, both for the treatment of the fracture and for the prophylaxis of a fracture at another, in particular an adjacent, site, e.g., the adjacent vertebra or the adjacent vertebrae. In this case, use is made of the advantage that anesthesia has already taken place. The combination of the invention can also be used in classical vertebroplasty and/or kyphoplasty.

The invention also relates to the use of collagen, additional peptide, a calcium-containing substance and a crosslinker for producing a medical product or pharmaceutical preparation for the treatment and/or prophylaxis of osteoporosis and/or prophylaxis and treatment of bone fractures, where the crosslinker comprises a terminally functionalized oligolactone and preferably a catalyst. A further possible use is in the area of dentistry, e.g. for the bonding of inlays and crowns or for buildup fillings. Elastic fixing of root pins is also possible with the combination of the invention, instead of classical "sealer" based on methyl methacrylates or glass ionomer cements.

In relation to the components preferably used, to avoid repetition, reference is made to the above statements concerning the combination of the invention, which apply here equally.

The invention further provides an in vitro method for producing artificial bones, bone parts, teeth, implants or implant coatings, in which the above-described components of the combination are brought into contact with one another and into the desired shape. In particular, in this method, the components are mixed together and used to fill a mold and set after crosslinking. Alternatively, a collagen-containing matrix of the desired shape can be brought into contact with the other components.

The invention also relates to an artificial bone, an artificial bone part, an implant, in particular an implant for stabilizing bone fractures, or an implant coating, which can be obtained by the method of the invention described above. Artificial teeth, crowns or inlays are also understood to be implants in the context of the invention.

A particular advantage of the present invention is that the artificial bone substance obtained after the crosslinking is very biocompatible. The initial setting phase, associated with high adhesive properties, and the slow absorption in the body as healing processes progress, is a further advantage.

The invention is explained below by means of examples. The following examples serve to illustrate the subject matter of the invention by way of example, but the invention is not restricted to the examples mentioned.

EXAMPLES

Example 1

Liquid Bone with Ethylene Glycol Oligolactide with Terminal Isocyanate Groups A particularly stable adhesive for stabilizing bone was prepared with ethylene glycol oligolactide with terminal isocyanate groups (EOL-NCO) as bridge molecule.

Reaction Scheme 2:

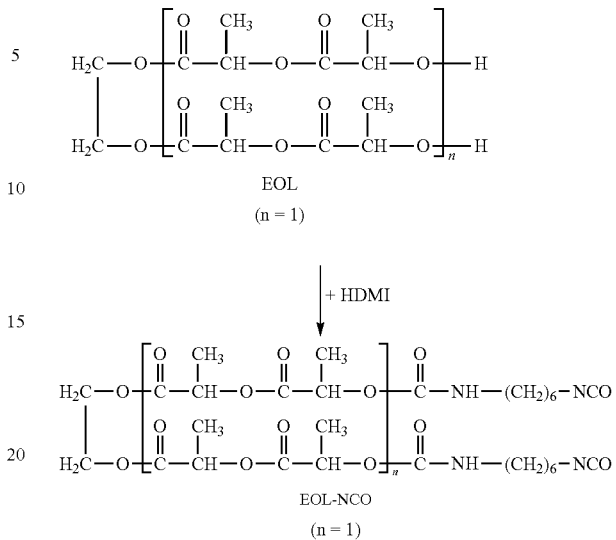

Ethylene glycol oligolactide (EOL) was reacted in accordance with reaction scheme 2 with hexamethylene diisocyanate (HMDI). The reaction product was EOL-NCO (ethylene glycol oligolactide with terminal isocyanate groups) which was employed as bridge molecule in the adhesive.

To set the adhesive, EOL-NCO in dimethyl sulfoxide (DMSO) and a mixture of oligopeptide (a polymer of tyrosine and lysine, see example 2) and 1,4-diaza[2.2.2]bicyclooctane (DABCO®) as catalyst, likewise in DMSO as solvent, is brought into contact with one another and with a mixture of collagen and a calcium-containing substance.

Example 2

The components employed in this experiment were collagen, oligopeptide 1 (amino acid sequence composed of lysine and tyrosine, preferably using an oligopeptide of n=5 to n=10, ethylene glycol oligolactide with terminal isocyanate groups (EOL-NCO) and 1,4-diaza[2.2.2]bicyclooctane (DABCO®) as catalyst, DMSO as solvent, and hydroxylapatite.

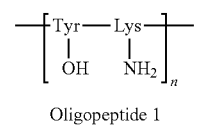

Oligopeptide 1

Preparation of EOL-NCO

Ethylene glycol oligolactide (1/2, i.e. reaction of 1 part of ethylene glycol with 2 parts of lactide in the ring-opening polymerization, n=1) was reacted with hexamethylene diisocyanate (HDI) (see reaction scheme 2), and the reaction resulted in EOL-NCO (ethylene glycol oligolactide with terminal isocyanate groups) which was used in the further experiments described.

Reaction Scheme 2:

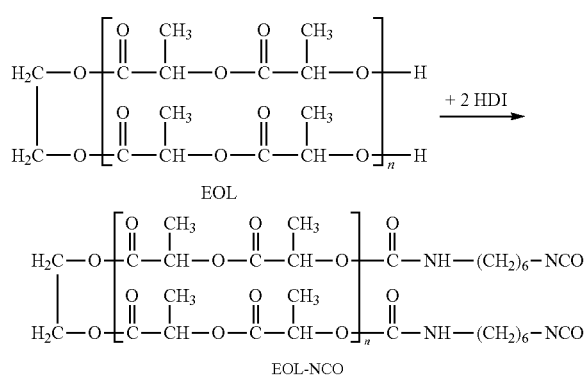

EOL

Mixing the Components:

The setting was carried out with the system EOL-NCO in dimethyl sulfoxide (DMSO) (component 1) and hydroxylapatite/peptides/1,4-diaza[2.2.2]bicyclooctane (DABCO®) as catalyst in DMSO (component 2) (reaction scheme 3).

Reaction scheme 3:

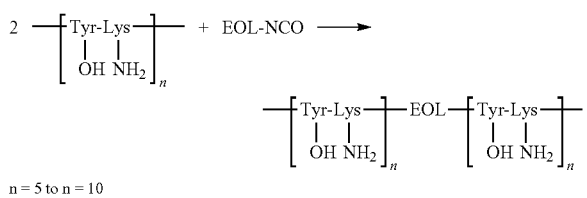

n = 5 to n = 10

The structure of the polymer is depicted only diagrammatically, with the crosslinking being shown not in relation to collagen but in relation to the additional peptide. It is assumed in this case that the reaction of EOL-NCO takes place with the primary amino groups and hydroxyl groups of the peptide.

The following mixing ratio was tested: EOL-NCO/peptides 4.7/1 (w/w) and EOL-NCO/DABCO® 12.5/1 (w/w).

Example 3

Fixing of Implants

Prostheses of the hip, knee and shoulder are bolted into the hollow bone with a solid, structural component after the bone tissue has been resected and thus an aperture exists in the bone. In this case, interlocking is possible and, where appropriate, requires no additional fixing aids. If positive locking cannot be achieved, or immediate use of the implant is desired, prostheses in the hollow bone are provided with a cement coating of the preparation of the invention.

In this case, after rasping of the medullary cavity, in which most of the bone marrow is removed, collagen, where appropriate, additional peptide, calcium-containing substance and crosslinker are blended and injected by the operator into the bone, or more exactly, into the hollow medullary cavity of the bone. While still in the liquid state, the prosthesis is then introduced and is then fixed by the process of setting of the bone adhesive. The operator waits for the 2-10 minutes this process takes and then continues the operation.

Example 4

Prophylaxis of Fractures

In order to stabilize brittle bone without fracture, it is perforated—similar to vertebroplasty—with a drill or a sharp needle. The location of the needle is checked with an X-ray picture. The liquid bone is then stirred as in example 1 or 2 and applied in liquid form into the bone. In this case, too, it may also be necessary, where appropriate, for the medullary cavity to be prepared, but this should not be the primary aim. On the contrary, the pasty bone should now be distributed in the medullary cavity where there is little bone substance, and set there. The result of distribution is also checked by X-ray. The introduced needle must be removed before the cement can set. The operation can be carried out under local anesthesia or general anesthesia. Sterile conditions must be observed during every operation.

The invention claimed is:

1. A kit for the treatment of osteoporosis and/or treatment of bone fractures or for the fixing of an implant, comprising the components:
   collagen in a proportion of 10-70% by weight,
   an additional peptide up to 40% by weight, wherein the additional peptide comprises at least two reactive amino groups and/or hydroxyl groups,
   a calcium-containing substance in a proportion of 20-90% by weight, and
   a crosslinker in a proportion of 0.05 to 40% by weight, wherein the crosslinker comprises a terminally functionalized oligolactone.

2. The kit of claim 1, wherein the calcium-containing substance is calcium phosphate.

3. The kit of claim 2, wherein the calcium phosphate is hydroxylapatite.

4. The kit of claim 1, wherein the oligolactone is an ethylene glycol oligolactone.

5. The kit of claim 1, wherein the oligolactone has terminal isocyanate groups.

6. The kit of claim 1, wherein the crosslinker further comprises a catalyst of the crosslinking reaction.

7. The kit of claim 6, wherein the catalyst comprises a strongly basic amine, amidine, tertiary amine and/or alkanolamine.

8. The kit of claim 1, wherein the peptide comprises at least one diamino acid.

9. The kit of claim 8, wherein the peptide is a lysine-containing peptide.

10. The kit of claim 1, wherein 40-60% of the amino acids of the additional peptide are lysine and/or 40-60% of the amino acids of the additional peptide are tyrosine.

11. The kit of claim 1, wherein the additional peptide is an oligopeptide with a length of 10-20 amino acids, wherein 40-60% of amino acids are lysine and/or 40-60% of amino acids are tyrosine, wherein the calcium-containing substance is hydroxylapatite, and wherein the crosslinker comprises an ethylene glycol oligolactide having terminal isocyanate groups and 1,4-diaza[2.2.2]bicyclooctane.

12. The kit of claim 1, wherein one or more of the components are taken up in a solvent.

13. The kit of claim 12, wherein the solvent is a phosphate buffer and/or DMSO.

14. A composition prepared by mixing the components of the kit of claim 1, wherein the collagen is crosslinked.

15. The composition of claim 14, wherein the composition is in the form of an artificial bone, bone part, implant or in the form of an implant coating.

16. The composition of claim 15, wherein the implant is a nail, a plate, a screw, a pin, a prosthesis, a hip socket, a cage or a vertebra replacement.

17. A medical product, comprising the kit of claim 1.

18. A method for producing a medical device for the treatment of osteoporosis and/or treatment of bone fractures, comprising bringing the components of the kit of claim 1 together and bringing them into contact with a bone and/or an implant.

19. A method for producing a medical product for fixing an implant, comprising bringing the components of the kit of claim 1 together and bringing them in contact with the implant.

20. A method for the in vitro preparation of artificial bones, bone parts, implants or implant coatings, comprising bringing the components of the kit of claim 1 into contact with one another and bringing them into a desired shape.

21. The kit of claim 1, wherein the additional peptide is in a proportion of 10-30% by weight.

* * * * *